(12) United States Patent
Obsuth (10) Patent No.: US 8,663,266 B1
(45) Date of Patent: Mar. 4, 2014

(54) DEVICE AND METHOD TO PROTECT NEEDLE LOCALIZATION WIRE

(76) Inventor: Danette M. Obsuth, Oak Ridge, NJ (US)

( * ) Notice: Subject to any disclaimer, the term of this patent is extended or adjusted under 35 U.S.C. 154(b) by 672 days.

(21) Appl. No.: 12/118,478

(22) Filed: May 9, 2008

Related U.S. Application Data (60) Provisional application No. 60/928,574, filed on May 9, 2007.

(51) Int. Cl.
*A61B 17/34* (2006.01)

(52) U.S. Cl.
USPC .......................................... 606/185; 604/116

(58) Field of Classification Search
USPC ........... 606/167, 185, 562, 565; 604/116, 272
See application file for complete search history.

(56) References Cited

U.S. PATENT DOCUMENTS

| | | | |
|---|---|---|---|
| 5,074,847 A | 12/1991 | Greenwell et al. | |
| 2004/0049159 A1 | 3/2004 | Barrus et al. | |
| 2004/0138602 A1 * | 7/2004 | Rossen | 602/41 |
| 2005/0113759 A1 | 5/2005 | Mueller, Jr. et al. | |
| 2007/0088281 A1 | 4/2007 | Ritchey | |
| 2007/0106222 A1 | 5/2007 | Bennett | |

* cited by examiner

*Primary Examiner* — Victor Nguyen
(74) *Attorney, Agent, or Firm* — Law Offices of Mitchell P. Novick; Benjamin Appelbaum (57) ABSTRACT

A wire protector to cover an exposed portion of a device inserted into an organism comprises a removable backing layer removably joined to an attachment layer, and a transparent covering layer. The wire protector has a first end and a protector strip, the first end including a site wall and a connector wall, the site wall defining an insertion site therein, the site wall further comprising one or more prongs, the prongs facing the insertion site, the protector strip comprising one or more strip walls, such that when the backing layer is removed from the attachment layer, first end is positioned over the device insertion site, the protector strip is positioned over the exposed portion of the device, the protector device covers the exposed device portion. The wire protector stabilizes and protects needle localization wires used in breast biopsies, and can be used for other implanted devices. Also disclosed is a method for covering such exposed portion of such inserted device.

3 Claims, 9 Drawing Sheets

DEVICE AND METHOD TO PROTECT NEEDLE LOCALIZATION WIRE

CROSS REFERENCES TO RELATED APPLICATIONS

This application claims the benefit of United States Provisional Application For Patent Ser. No. 60/928,574, filed 9 May 2007, the contents of which are incorporated by reference herein in their entirety.

FIELD OF THE INVENTION

The field of this invention is a device and method for the protection of a needle localization wire, and more specifically, such a wire that is used in the diagnosis and treatment of breast cancer. Generally, a wire is inserted into a patient's breast to mark the location of a suspicious growth, and a length of the wire is left outside the breast where it remains for a time period between insertion and removal. During this time period, the exposed wire needs to be covered, to maintain the inserted wire in a proper position, and to protect the insertion site from potential infection. Embodiments of the present invention cover the insertion site and the exposed wire, allowing medical personnel to see the insertion site and the wire.

BACKGROUND OF THE INVENTION

Mammography is a procedure commonly used for the detection of breast cancer. Should a suspicious growth be detected, a step in diagnosis and treatment involves either a biopsy of the growth, and/or its removal. Depending upon the type and size of the growth, and whether or not it has spread elsewhere in the body, other treatments, ranging from additional surgery, chemotherapy and radiation may be involved. However, in order to perform either a biopsy, or removal of the growth, it is important to know where the growth is within the affected tissue.

Current techniques involve the insertion of one or more needle localization wires into the breast, to direct a surgeon to the affected area. The wires are inserted using a needle, and generally with the aid of X-rays. After the wire has been inserted, the needle is removed and a wire is left in place, with a portion of the wire remaining outside of the breast.

This needle localization wire is placed in the breast during mammography and should be protected during the time period between insertion and surgery. The wire should be stabilized, such that it will not move, during this time period. It is also important to secure the implanted wire to the patient such that it will not advance further into the breast, or pull out, complicating the situation and potentially causing harm to the patient. During this time period, the exposed wire needs to be covered, to maintain the inserted wire in a proper position, and to protect the insertion site from potential infection. Embodiments of the present invention cover and protect the wire.

In the prior art, there are no devices that perform this protective function. Prior art protection include the following options: (1) using gauze and medical tape to secure the wire in a number of ways, (2) taping the wire to the patient's skin, (3) using gauze taped to the patient's breast, (4) using a material such as Tegaderm to cover the wires, and (5) using a paper or plastic cup to cover the wires, and taping the cup to the breast.

Embodiments of the present invention are made from a transparent material, such that medical personnel can see the wire's location through the wire protector. Visibility of the wire aids a surgeon or other medical personnel in removing this device without dislodging the wire from its location.

Embodiments of the present invention further comprise channels to allow secretions to flow away from the wire, again improving visibility of the wire.

The length of the wire protector device is long enough to cover the longest needle localization wire in use (currently, approximately 20 cm). To accommodate shorter wires, the device may be cut with a scissors, and a tab placed at the cut end to facilitate removal of the device.

BRIEF SUMMARY OF THE INVENTION

An object of the present invention is to provide a device that can effect localization wire security in a safe and professional manner.

Another object of the present invention is to provide a clear and unobstructed view of wire during imaging procedures, such as using X-rays.

In one example of current practice, two images are taken of a breast after the wire has been inserted to its proper position. The wire needs to be secured both to maintain it in place, yet be out of the way so that the images can be more accurately reviewed by medical personnel.

Yet another object of the present invention is to provide a wire protector device that will prevent obscuring of excess wire over the area of interest on the patient's body.

Another object of the present invention is to provide a wire protector device that is narrow enough to permit for multiple placement of wires, within a close vicinity of each other, without overlapping.

The device eliminates messy make-shift dressing combinations (e.g., gauze, tape, Tegaderm®)).

Another object of the present invention is to provide a cost effective, easy to use device that can be used to protect localization wires, catheters and the like, after their insertion into an organism.

Still another object of the present invention is to provide a kit for protecting localization wires, catheters and the like, that have been inserted into an organism.

This device comprises a special tab at the end of the wire protector which permits the surgeon to remove the device while working towards the entrance site, thereby enabling the surgeon to secure the wire as surgery progresses.

BRIEF DESCRIPTION OF THE SEVERAL VIEWS OF THE DRAWING

FIG. 10A-G illustrate usage of an embodiment of the present invention.

DETAILED DESCRIPTION OF THE INVENTION

Embodiments of the present invention are devices for the protection of a needle localization wire. This device protects the needle localization wire that is placed in the breast as a locator for the surgeon when a suspicious finding has been detected and is to biopsied and/or be removed.

Figure 1:
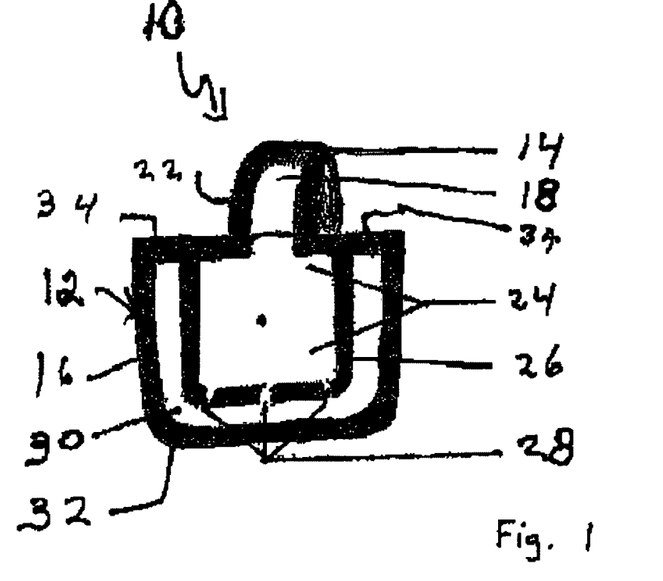
FIG. 1 is a schematic top view of a first embodiment of the present invention.
Figure 2:
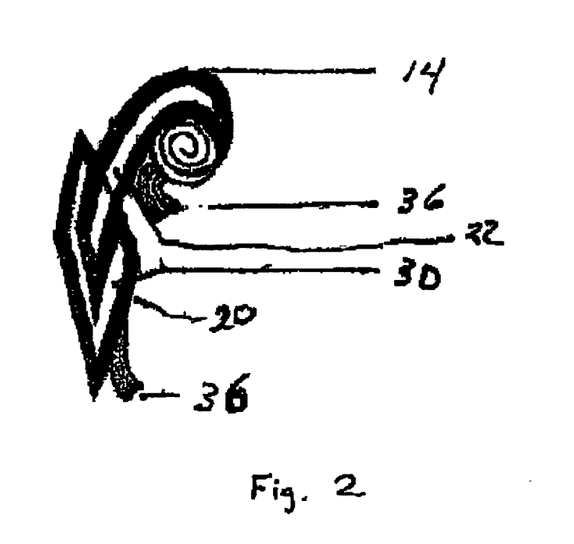
FIG. 2 is a schematic side view of the embodiment shown in FIG. 1.

A first embodiment 10 is shown in FIG. 1. Wire protector 10 comprises a first end 12 connected to tail section or protector strip 14, which is shown in a rolled-up configuration (FIGS. 1-2). The terms tail section and protector strip will be used interchangeably to describe this part of the wire protector device, in all of the embodiments. Both the first end 12 and the protector strip 14 each have a top surface 16 and 18, respectively, that will be exposed to the environment during use, and a bottom surface, 20 and 22, respectively, that will be in contact with the skin of the patient. FIG. 1 is shown with the top surfaces 16 and 18 facing the reader.

In this embodiment, the first end 12 has a D-shaped configuration, and comprises a wire site region 24 which is bordered by site wall 26. A plurality of channels 28 within site wall 26 provide a means for secretions, such as blood, bodily fluids or the like, that have exited the wire localization site on the patient, to escape, and be retained within reservoir 30, allowing for the clear visualization of the wire. The wire site region 24 is of sufficient size to enable a piece of gauze sponge 62 (optional, see FIG. 10C) to be positioned atop the wire localization site, if desired.

The reservoir 30 is bordered on several sides by a reservoir wall 32, which along with site wall 26, joins connector walls 34 to form the first end 12.

Although the first end 12 in this and the other embodiments is described as being D-shaped, it is to be understood that variations in this configuration, ranging from being rounded, oval, square, or other geometric shapes are expressly contemplated as being within the scope of this invention. The D-shape may aid in handling of the device, but the device's function is to cover the wire insertion site and provide a visible means of monitoring the position of the inserted wire.

Figure 3:
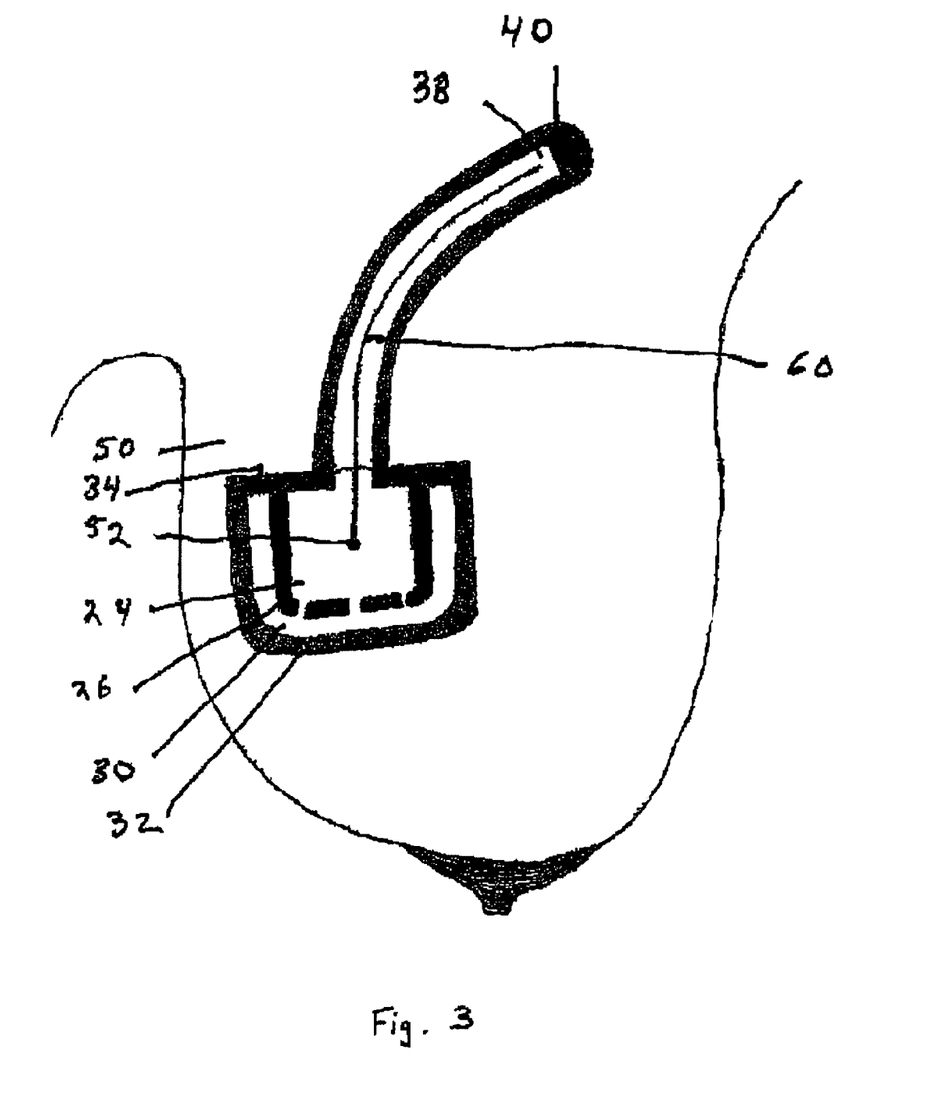
FIG. 3 is a schematic view of the embodiment shown in FIG. 1 while in use.

In use, the layer of backing material 36 is peeled away from the protector device 10, exposing a layer of adhesive attached to the bottom surface 20, 22 of the first end 12 and protector strip 14, respectively. The first end 12 is placed over the wire localization site 52 on the breast 50, and adhered to the skin by pressure. The wire protector 14 is unrolled, and the backing 36 removed, while guiding the wire 60 in the desired direction, working away from the wire localization site 52 (FIG. 3). The distal end of the unrolled wire protector 14 is a second end 38, which terminates as a tab 40. The length of wire 60 exposed will vary, depending upon factors such as, but not limited to, the length of wire that is inserted to the target growth, the external length needed to stabilize the wire between insertion and removal, and preferences of attending medical personnel. Before the surgical procedure, the wire protector 10 is removed, starting with tab 40 and working back to the wire insertion site 52.

For the purposes of this specification, the terms "distal" and "proximal" will refer to the location of the component in relation to where the localization wire in inserted into the patient. Thus, a proximal element of the device is close to where the wire is inserted; a distal element of the device is further away from where the wire is inserted.

Figure 4:
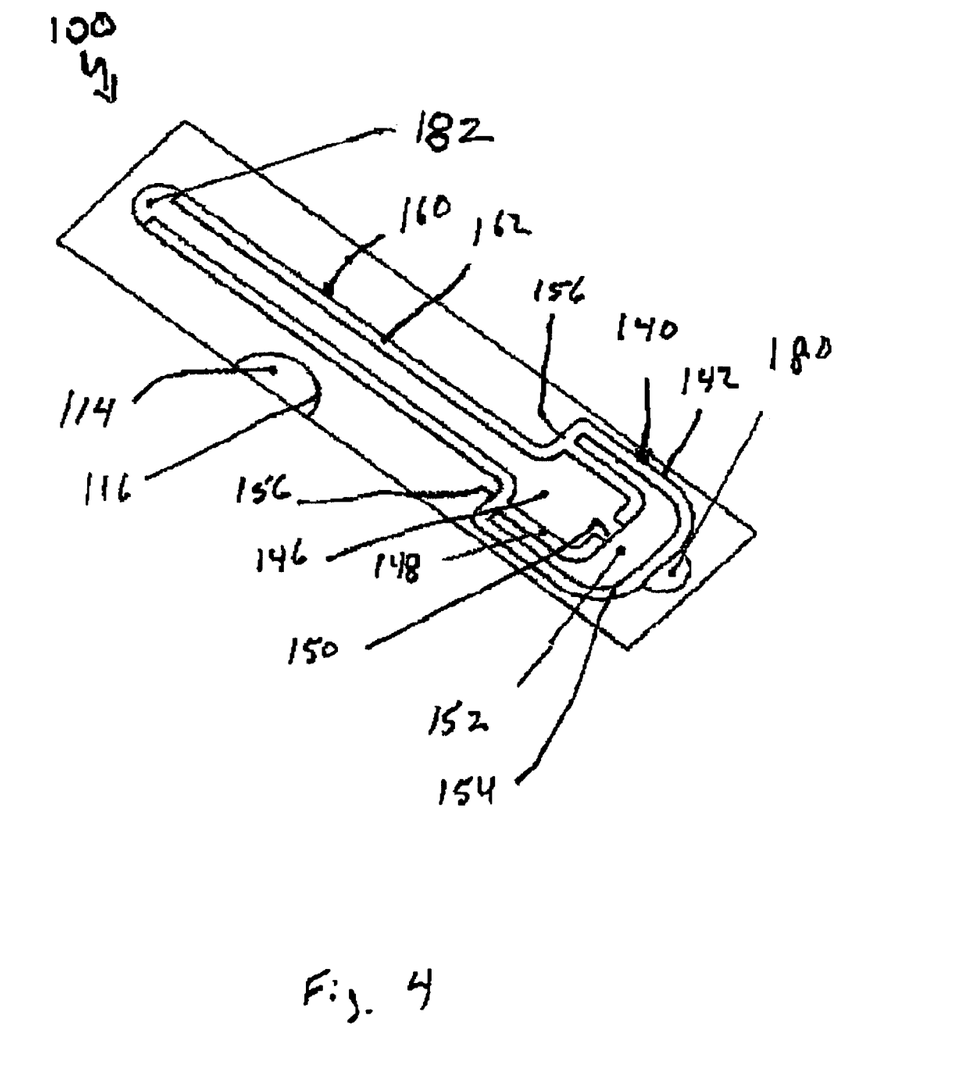
FIG. 4 is a schematic top view of a second embodiment of the present invention.
Figure 5:
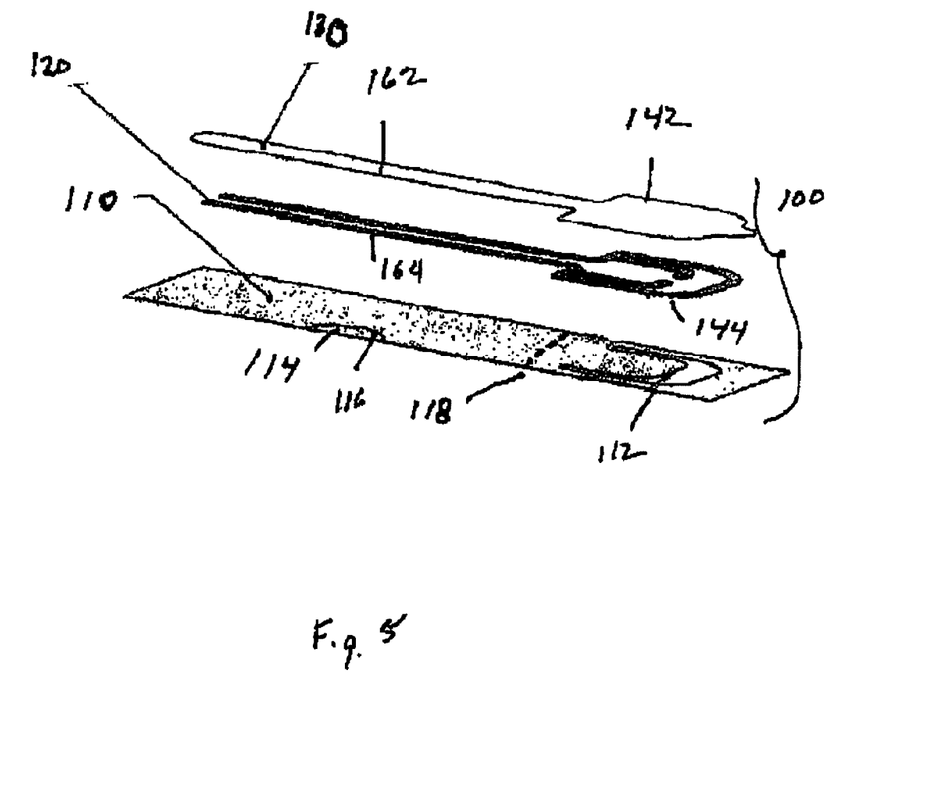
FIG. 5 is an exploded view of the embodiment shown in FIG. 4.

A second embodiment 100, in a flat configuration, is shown in FIGS. 4 and 5. Wire protector 100 is manufactured from several layers, a liner layer 110, a tape layer 120 and a film layer 130, which are attached to the tape layer 120. The tape layer comprises a strip of double-sided foam tape 120, shaped as shown in FIGS. 4-5. The film layer 130 comprises a layer of clear urethane film, providing a transparent surface so that the location of the wire 60 underneath the wire protector 100 can be seen.

The liner layer 110 includes a section 112 that is removed during the manufacturing process, in order to form part of the fluid reservoir 152 in the wire protector 100. The liner layer 110 is a standard silicone coated paper that will be removed from the wire protector device 100 during use. The material used for the liner layer 110 is known to those skilled in the art, and will not be described further; this is the same material used as the liner in all of the embodiments of the present invention.

Liner layer 110 also includes a perforated section 114 that can be used as an additional tab. When the wire protector 100 is too long, and the tail section 160 is trimmed, tab 182 is removed. By removing perforated section 114 from the liner along perforations 116, perforated section 114 is attached to the distal end of the remaining tail section 160, where it then functions as a replacement tab. Liner layer 110 includes a perforated region 118 that extends across the width of the liner layer 110 at a region below where the protector strip 160 connects to the first end 140.

The tape layer 120 comprises a strip of a double sided foam tape, formed to the desired configuration. In certain embodiments, the tape layer 120 ranges in thickness from about 5 mil to about 50 mil; in other embodiments it ranges in thickness from about 10 mil to about 40 mil, and in other embodiments ranges in thickness from about 15 mil to about 30 mil.

The film layer 130 comprises a strip of a clear urethane film, formed to a configuration where it covers and overlaps the tape layer 120. In certain embodiments, the film layer 130 ranges in thickness from about 1 mil to about 10 mil; in other embodiments it ranges in thickness from about 1 mil to about 5 mil, and in other embodiments it ranges in thickness from about 1 mil to about 3 mil.

Although not discussed in relation to the first embodiment 10 (FIGS. 1-2), first embodiment 10, and the other embodiments shown herein, are manufactured from the same layers and materials as described for the second embodiment, although the configuration and thickness of these layers may differ from that of the second embodiment 100 (FIGS. 4-5).

Wire protector 100 comprises a first end 140 connected to protector strip or tail section 160, which terminates in a tab 182. This tab 182, at the end of tail section 160, is removable. The terms tail section and protector strip will be used interchangeably to describe this part of the wire protector device, in all of the embodiments. Both the first end 140 and the protector strip 160 each have a top surface 142 and 162, respectively, that will be exposed to the environment during use, and a bottom surface, 144 and 164, respectively, that will be in contact with the skin of the patient. FIG. 4 is shown with the top surfaces 142 and 162 facing the reader.

First end 140 has a D-shaped configuration, and comprises a wire site 146 which is bordered by site wall 148. A channel 150 within site wall 148 provides a means for secretions, such as blood, bodily fluids or the like, that have exited the wire localization site 52 on the patient, to escape, and be retained within reservoir 152, which is bounded by reservoir wall 154. The wire site 146 is of sufficient size to enable optional gauze sponge 62 (see FIG. 10C) to be positioned atop the wire localization site 52, if desired. A tab 180 is attached along the first end 140 and aids in handling of the wire protector during use.

The reservoir 152 is bordered on several sides by reservoir wall 154, which along with site wall 148, joins connector walls 156 to form the first end 140.

Figure 6:
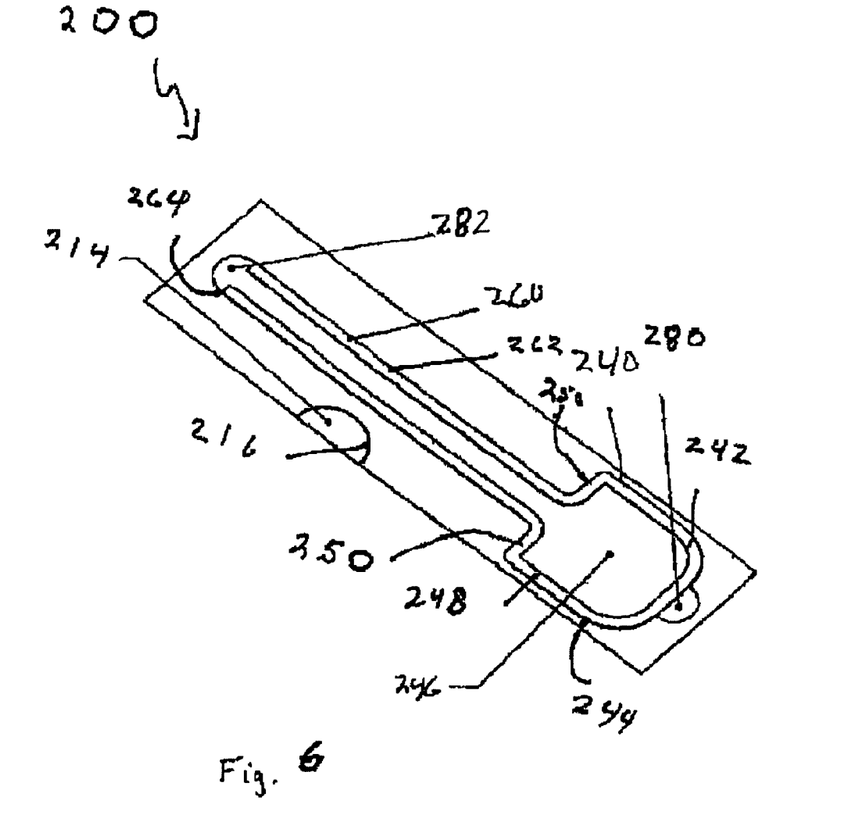
FIG. 6 is a schematic top view of a third embodiment of the present invention.
Figure 7:
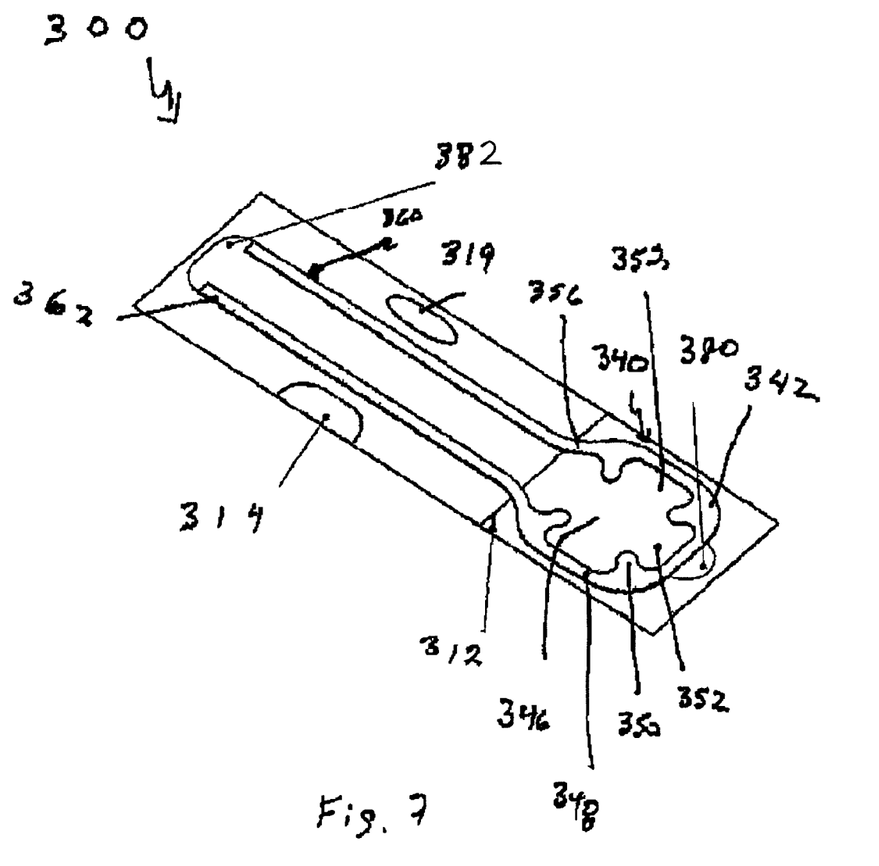
FIG. 7 is a schematic top view of a fourth embodiment of the present invention.

A third embodiment 200 is shown in FIGS. 6 and 7. Wire protector 200 is manufactured from several layers, and has essentially the same structure and configuration as the second embodiment (FIGS. 4-5), except that the wire site region is larger than in the second embodiment; no channel for secretions is present.

The liner layer includes a perforated section 214 that can be used as an additional tab. When the wire protector 200 is too long, and the tail section 260 is trimmed, tab 282 is removed. By removing perforated section 214 from the liner along perforations 216, perforated section 214 can be attached to the distal end of the remaining tail section 260, where it becomes a replacement tab.

Wire protector 200 comprises a first end 240 connected to protector strip or tail section 260, which terminates in a tab 282. The terms tail section and protector strip will be used interchangeably to describe this part of the wire protector device, in all of the embodiments. Both the first end 240 and the protector strip 260 each have a top surface 242 and 262, respectively, that will be exposed to the environment during use, and a bottom surface, 244 and 264, respectively, that will be in contact with the skin of the patient. FIG. 6 shows the top surfaces 242 and 262 facing the reader.

First end 240 has a D-shaped configuration, and comprises a wire site 246 which is bordered by site wall 248. The wire site 246 is of sufficient size to enable a gauze sponge 62 (optional, see FIG. 10C) to be positioned atop the wire localization site 52, if desired. A tab 280 is attached along the first end 240 and aids in handling of the wire protector during use.

The wire site 246 is bordered on several sides by site wall 248, which joins connector walls 250 to form the first end 240.

Figure 8:
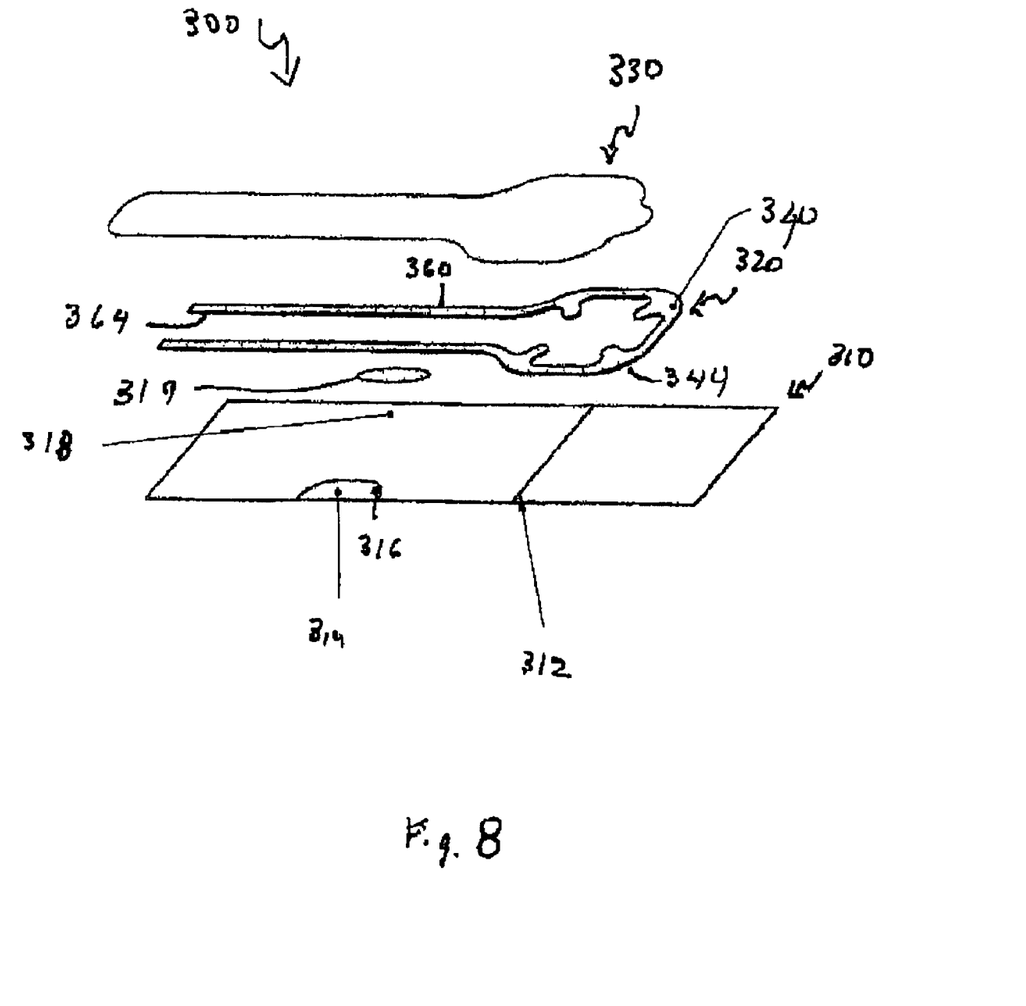
FIG. 8 is an exploded view of the embodiment shown in FIG. 7.

A fourth embodiment 300 (FIGS. 7-9) is manufactured from several layers, a liner layer 310, a tape layer 320 and a film layer 330, which are attached to the tape layer 320. The tape layer comprises a strip of double-sided foam tape 320, cut out as shown in FIGS. 7-8. The film layer 330 comprises a layer of clear urethane film, providing a transparent surface so that the location of the wire 50 underneath the wire protector 300 can be seen.

The liner layer 310 is a standard silicone coated paper that will be removed from the wire protector device 300 during use. The material used for the liner layer 310 is known to those skilled in the art, and will not be described further; this is the same material used as the liner in all of the embodiments of the present invention. Liner layer 310 includes a perforated region, shown at 312 which extends across the width of the liner layer 310 at a region below where the protector strip 360 connects to the first end 340.

Liner layer 310 also includes a section 314 that can be used as an additional tab. When the wire protector 300 is too long, and the tail section 360 is trimmed, tab 382 is removed. By removing section 314 from the liner along cut region 316, section 314 can be attached to the distal end of the remaining tail section 360, where it becomes a replacement tab. Liner layer also includes an attachment region 318 where an adhesive foam strip 319, which is used to tack down the end of the wire 50, is attached.

The tape layer 320 comprises a strip of a double sided foam tape, formed to the desired configuration. In certain embodiments, the tape layer 320 ranges in thickness from about 5 mil to about 50 mil; in other embodiments it ranges in thickness from about 10 mil to about 40 mil, and in other embodiments ranges in thickness from about 15 mil to about 30 mil.

The film layer 330 comprises a strip of a clear urethane film, formed to a configuration where it covers and overlaps the tape layer 320. In certain embodiments, the film layer 330 ranges in thickness from about 1 mil to about 10 mil; in other embodiments it ranges in thickness from about 1 mil to about 5 mil, and in other embodiments it ranges in thickness from about 1 mil to about 3 mil. An example of a film used for this layer is COTRAN® 9702 (Registered trademark of 3M Company, St. Paul, Minn. for what the manufacturer describes as a controlled caliper ethylene vinyl acetate membrane for use in the fabrication of transdermal, topical and transmucosal drug-delivery systems. This material is also described as being heat sealable and able to be laminated directly to adhesives). Other materials having comparable properties could also be used.

Wire protector 300 comprises a first end 340 connected to protector strip or tail section 360, which terminates in a tab 382. The terms tail section and protector strip will be used interchangeably to describe this part of the wire protector device, in all of the embodiments. Both the first end 340 and the protector strip 360 each have a top surface 342 and 362, respectively, that will be exposed to the environment during use, and a bottom surface, 344 and 364, respectively, that will be in contact with the skin of the patient. FIG. 7 is shown with the top surfaces 342 and 362 facing the reader.

First end 340 has what can best be described as an internal clover-leaf configuration, and comprises a wire site 346 which is bordered by site wall 348. The wire site 346 is made to a size such that a piece of gauze sponge 62 (FIG. 10C) can be positioned atop the wire localization site, if desired, without interfering with adhesion of the device to the patient. A tab 382 is attached along the first end 340 and aids in handling of the wire protector during use.

Site wall 348 is configured such that it has a plurality of extensions or prongs 350 that extend from the site wall 348 towards the wire site 346. The prongs 350 serve to retain a gauze sponge; prongs 350 can be moved away from the film layer 330 and a gauze sponge 62 positioned therebetween. The device can be used without a gauze sponge and form the walls of reservoirs 352 that will allow for the accumulation of secretions from the wire insertion site 52 to accumulate away from the wire 60. The prongs 350 can be moved away from contact with the film layer 330 and then be used to hold a gauze sponge 62 in place. Site wall 348 becomes connected to strip protector wall 362 by means of connector wall 356.

Embodiments of the present invention may be packaged as individual units, or as part of a kit. Such a kit could comprise one or more wire protector devices, and one or more gauze sponges, or comparable materials. Kits could be supplied either in sterile or non-sterile packaging.

In one embodiment, an individual wire protector device 300 is packaged in a peel-type package 400, between a sheet of TYVEK® (Registered trademark of E.I. DuPont de Nemours & Co., Wilmington, Del.) 410 as a package bottom, and a sheet of clear polyester 420 (FIG. 9) with a layer of adhesive therebetween. The TYVEK® layer 410 will generally include indicia 412, such as product identification information and directions for use, either on the inside (FIG. 9) or the outside of the package. The package can be provided either as a non-sterile or sterile package.

Figure 9:
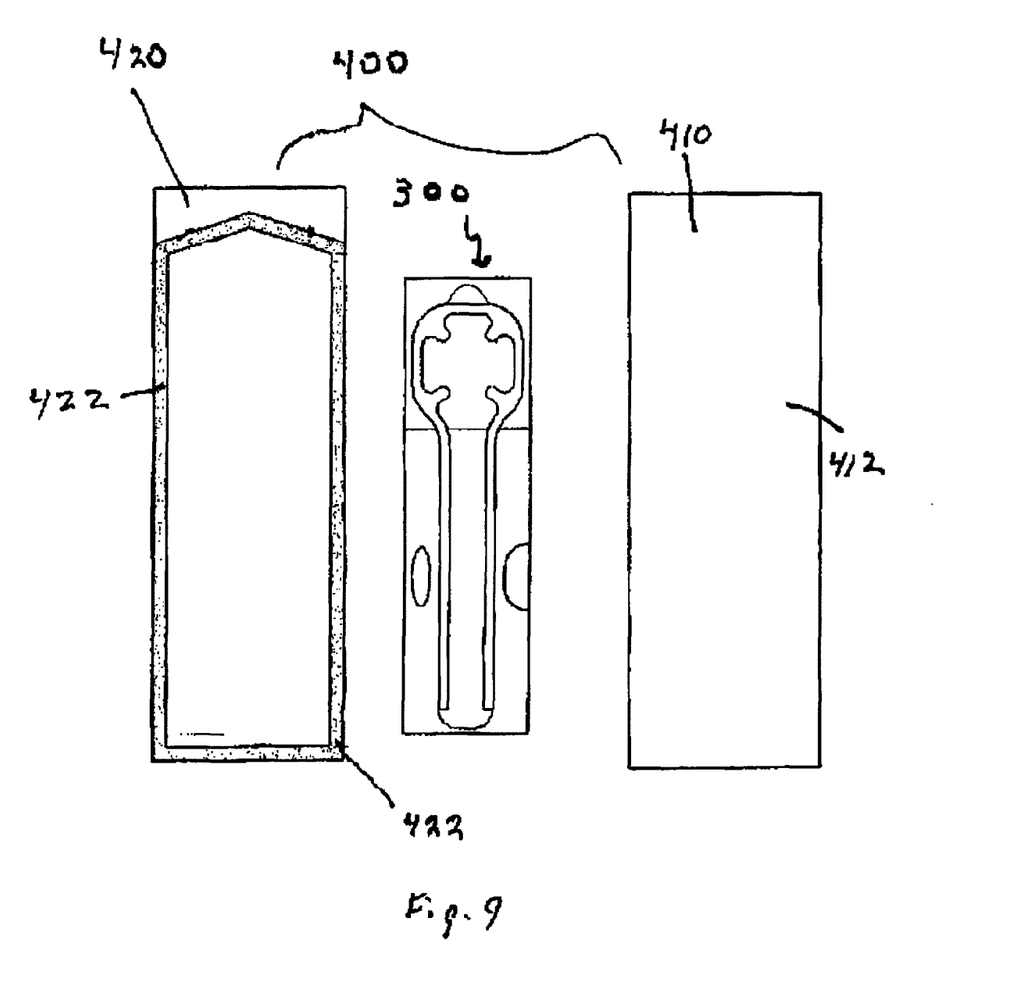
FIG. 9 is a schematic view of the embodiment shown in FIG. 7, in an exploded view of the packaging.

Reference numeral 422 refers to a region of the packaging that is used for sealing it; this region generally will be a layer of adhesive material, but could include other means for sealing peel-apart packages, such as, for example, heat-sealing, or other methods known to those skilled in the art. As seen in FIG. 9, sealing region 422 surrounds the wire protector device 300 within the package 400. The TYVEK® sheet and polyester employed for the packaging are materials commonly known to those skilled in the art, and will not be described further. Units supplied in non-sterile packages can be sterilized using methods known to those skilled in the art.

Figure 10:
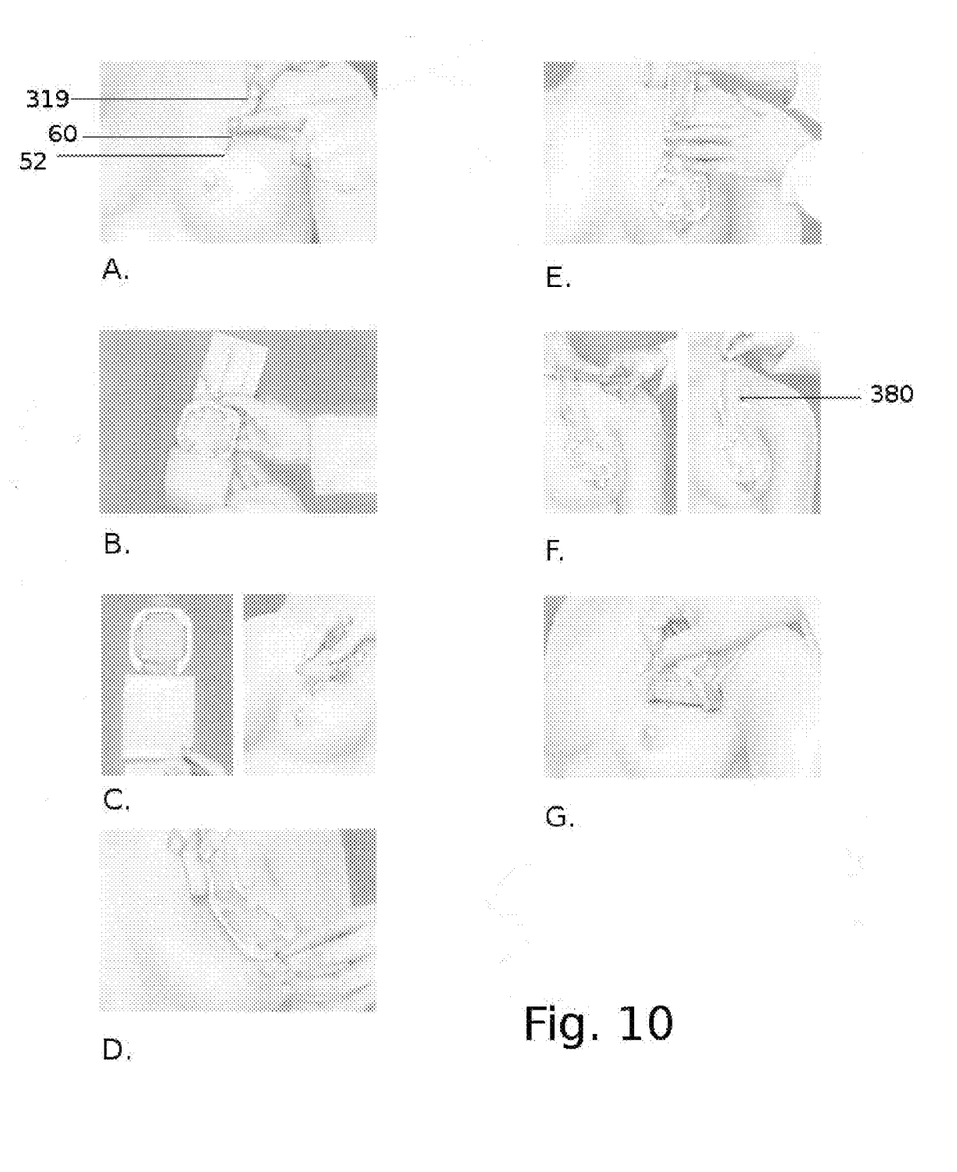

Instructions for use of embodiments of the present invention are schematically illustrated in FIG. 10. Initially, after the localization wire has been inserted within the patient, the free end of the wire 60 is tacked down, using tab 319. The remainder of the package is then partially opened, by removing the paper backing away from the square first end 340 to the perforated line 312 on the liner.

In this embodiment, which includes a sterile gauze pad, the gauze pad 62 is applied to cover the wire insertion site on the patient. The gauze pad can be applied either directly to the wire insertion site, or held in place by means of extension tabs or prongs 350 at the wire protector's first end. The square patch section is then placed over the wire insertion site on the patient, and pressure is applied on the section to adhere it to the skin.

The remaining paper backing is removed from the wire protector device, and the see-through wire protector strip is positioned to cover and protect the wire, applying the adhesive edges to the skin, so that the wire protector strip stays in place.

If the user finds that the wire protector strip portion of the device is too long, the strip can be cut to the desired size using a scissor. The additional tab 314 that is part of the backing is then removed from the paper liner, and the tab 314 is applied to the end to facilitate removal of the wire protector device.

When it is time to remove the wire protector strip, the adhesive-free tab at either end can be used to assist with removal of the device.

Using any of the various embodiments described herein, medical personnel can see the wire's location through the wire protector strip. Visibility of the wire aids a surgeon or other medical personnel in removing the wire protector without dislodging the wire from its location.

The length of the wire protector embodiments is long enough to cover the longest needle localization wire currently in use (currently, approximately 20 cm). To accommodate shorter wires, the wire protector may be cut with a scissors, and the semi-circular tab placed at the remaining end; this tab is removable when used with a shorter wire. Should longer length or wider width localization wires be used in the future, such longer length and/or wider width wires are expressly considered to be within the scope of this invention, and the size of the wire protector embodiments described herein scaled up accordingly.

While embodiments of the present invention have been described with use on human beings, it is to be understood that embodiments of the present invention could also be used to cover wires that are placed in other organisms, such as, but not limited to mammals such as farm animals (such as cows, horses, sheep), zoo animals (for example, lions, monkeys, zebras), domestic pets such as dogs and cats, and a range of other animals, literally from A through Z. Additionally, embodiments of the present invention could be used to cover other medical devices, such as catheters, cannulas, mediports, or the like, or other implanted devices that include an external lead or connection of some type, that may be utilized during various procedures, or to prevent an implanted device from being pulled out by an individual. These can include catheters for the intravenous infusion of medications and the like, for removal of blood or other bodily fluids, which can include procedures such as, but not limited to, cranial, digestive, intestinal, phlebotomy, urinary, veterinary and the like. For certain devices which may require a connection to an external source, such as to bag containing an intravenous solution, the wire protector strip can be cut with a scissors, and used to cover the device, omitting the addition of the spare tab to close off the distal end of the protector strip.

Other uses of embodiments of the present invention include providing waterproof coverage and added security to a site when a patient is not present at a medical facility, such as when radiation ports are implanted. Another use of embodiments of the present invention is to provide a waterproof covering at an incision site for other types of medical implants, such as wires, intravenous catheters and the like, as described previously. Regarding such other uses, these embodiments may comprise additional adhesive strips strategically placed to enhance further such waterproof coverage and/or added security; determining such strategic placement is well known in the prior art.

Although this invention has been described with a certain degree of particularity, it is to be understood that the present disclosure has been made only by way of illustration, and that numerous changes in the details of the composition, construction, and use may be resorted to without departing from the spirit and scope of the invention.

I claim:

1. A device protector to cover an exposed portion of a device inserted into an organism at a device insertion site, the device protector comprising:

a covering layer having a first end and a lower surface, the covering layer being generally transparent, the covering layer being positionable to cover the exposed portion of the device, the covering layer being longer than the attachment layer;

an attachment region generally along a perimeter of the lower surface of the covering layer, the attachment region being adhesively attachable to the organism around the device insertion site;

an opening in the first end large enough to accommodate passage of an end of the exposed portion;

a removable backing layer removably attached to the attachment region; the backing layer comprising a removable adhesive tab, the removable adhesive tab used to adhere the exposed section of the device to the organism;

the first end including a site wall and a connector wall, the site wall defining an insertion site region therein, the site wall further comprising one or more prongs, the prongs facing the insertion site region;

a protector strip comprising one or more strip walls, the strip walls each having a proximal end and a distal end, the strip walls disposed such that there is a gap therebetween, the strip walls proximal end joined to the connector walls;

such that when the backing layer is removed from the attachment layer, the first end positioned over the device insertion site, and the protector strip being positioned over the exposed portion of the device, the protector device covers the exposed device portion, the exposed device portion being visible through the protector device;

a tab, the tab being attached to the first end;

a second tab, the second tab being attached to the protector strip distal end; and the backing layer further comprising an additional removable tab, the additional removable tab being attached to the protector strip distal end after the device protector has been shortened.

2. A device protector to cover an exposed portion of a localization wire inserted within a living organism, the device protector comprising:
- a removable backing layer, the backing layer comprising a removable adhesive tab, the removable adhesive tab used to adhere the exposed portion of the localization wire to the organism;
- an attachment layer having a lower surface and an upper surface, the backing layer being removably joined to the lower surface;
- a covering layer joined to the upper surface, the covering layer being generally transparent and being longer than the attachment layer, the covering layer being positionable to cover the exposed portion of the localization wire;
- the device protector further comprising a first end and a protector strip;
    - the first end including a site wall and a connector wall, the site wall defining an insertion site therein,
    - the site wall further comprising one or more prongs, the prongs facing the insertion site;
    - a tab attached to the first end;
    - the protector strip comprising one or more strip walls, the strip walls each having a proximal end and a distal end, the strip walls disposed such that there is a gap therebetween, the strip walls proximal end joined to the connector walls;
- such that when the backing layer is removed from the attachment layer, the first end positioned over the wire insertion site, and the protector strip being positioned over the exposed portion of the localization wire, the device protector covers the exposed localization wire portion, and the exposed localization wire portion is visible through the device protector;
    - a second tab, the second tab being attached to the protector strip distal end; and
    - the backing layer further comprising an additional removable tab, the additional removable tab being attached to the protector strip distal end after the device protector has been shortened.

3. A device protector to cover an exposed portion of a device inserted into an organism at a device insertion site, the device protector comprising:
- a covering layer having a first end and a lower surface, the covering layer being generally transparent;
- an attachment region generally along a perimeter of the lower surface of the covering layer, the attachment region being adhesively attachable to the organism around the device insertion site;
- an opening in the first end large enough to accommodate passage of an end of the exposed portion;
- a removable backing layer removably attached to the attachment region, the backing layer comprising a removable adhesive tab, the removable adhesive tab used to adhere the exposed section of the device to the organism;
- a covering layer being longer than the attachment layer;
- a protector strip;
- the first end including a site wall and a connector wall, the site wall defining an insertion site region therein,
- the site wall further comprising one or more prongs, the prongs facing the insertion site region; and
- the protector strip comprising one or more strip walls, the strip walls each having a proximal end and a distal end, the strip walls disposed such that there is a gap therebetween, the strip walls proximal end joined to the connector walls; and
- a tab, the tab being attached to the first end;
- such that when the backing layer is removed from the attachment layer, the first end positioned over the device insertion site, and the protector strip being positioned over the exposed portion of the device, the protector device covers the exposed device portion, the exposed device portion being visible through the protector device; and
- a second tab, the second tab being attached to the protector strip distal end;
- wherein the backing layer further comprises an additional removable tab, the additional removable tab being attached to the protector strip distal end after the device protector has been shortened.

* * * * *